United States Patent [19]

Millheim et al.

[11] Patent Number: 5,012,674
[45] Date of Patent: May 7, 1991

[54] METHOD OF EXPLORATION FOR HYDROCARBONS

[75] Inventors: Keith K. Millheim; Houston B. Mount, II; Chandra S. Rai, all of Tulsa; Carl H. Sondergeld, Broken Arrow, all of Okla.

[73] Assignee: Amoco Corporation, Chicago, Ill.

[21] Appl. No.: 265,073

[22] Filed: Oct. 31, 1988

[51] Int. Cl.⁵ .............................................. E21B 49/02
[52] U.S. Cl. ...................................... 73/153; 324/377
[58] Field of Search .................... 73/38, 151, 152, 153, 73/821, 818, 825, 841, 845; 250/255; 324/201, 377

[56] References Cited

U.S. PATENT DOCUMENTS

| | | | |
|---|---|---|---|
| 2,104,743 | 1/1938 | Herrick | 324/377 |
| 2,414,550 | 12/1947 | Patch | 73/825 |
| 3,025,398 | 3/1962 | Dameron | 250/255 |
| 3,373,440 | 3/1968 | Jenkins et al. | 73/153 |

OTHER PUBLICATIONS

Telford et al., *Applied Geophysics*, Cambridge University Press, 1976, pp. 792–794 and 806–807.

Primary Examiner—Michael J. Tokar
Assistant Examiner—Kevin D. O'Shea
Attorney, Agent, or Firm—Scott H. Brown; Fred E. Hook

[57] ABSTRACT

A method of exploring for hydrocarbons is disclosed wherein core is obtained over substantially the entire length of a well and substantially all lithologies represented within the core are analyzed at a core analysis facility located adjacent the well. A measurement of a plurality of physical properties of the core are made promptly after the core is removed from the well. Thereafter, from the measurement of these physical properties, a depth correlated record is generated, and is used (a) to adjust the drilling plan for that well while it is being drilled, (b) used as inputs into other exploration processes, such as seismic surveys, magnetic surveys and gravity surveys, or (c) used for correlation with other depth correlated records obtained from other wells.

14 Claims, 7 Drawing Sheets

CONTINUOUS SAMPLE ANALYSIS

METHOD OF EXPLORATION FOR HYDROCARBONS

BACKGROUND OF THE INVENTION

1. Field of the Invention

The present invention relates to the exploration for hydrocarbons and, more particularly, to obtaining core from a wellbore and promptly analyzing the core at the well site to develop a better understanding of the earth's subsurface.

2. Description of the Prior Art

In the exploration for hydrocarbons, the search is concentrated on locating sedimentary rocks which have produced, contained or trapped hydrocarbons. To this end, first of all an understanding of the earth's subsurface is developed for a particular area of interest, usually from commercially available large area survey services. Such surveys can include gravity surveys, magnetic surveys and seismic surveys. Gravity and magnetic surveys are attractive because one can obtain large areal coverage for relatively minimal cost.

Problems with gravity and magnetic surveys are that each suffers from nonuniqueness, lack of resolution and each only provides an estimate of the relative thickness of material that lies above a layer of material with a higher density or magnetic response. Further, these surveys provide little information as to what type of material is below the subsurface or what is below the layer of material with the higher density or magnetic response. A problem with seismic surveys is that the traveltime between source initiation, reflection and receipt is known but the depth to the reflecting points is only an estimate based upon an assumed velocity that the seismic energy travels through each layer of the earth's subsurface. In any one velocity estimate is incorrect, then the depth estimates and the understanding of the subsurface can be greatly altered.

If the first understanding of the earth's subsurface indicates possible sediments, other sources of information are used to refine this understanding, such as geological descriptions of surface rocks and rock outcrops and subsurface information from any adjacent mines and/or previously drilled wellbores. From this refined understanding, a well location is made and drilling of the well is commenced. During and after the well has been drilled, a series of wireline wellbore logs are usually obtained, such as gamma ray, pulsed neutron and resistivity logs, that are used to estimate the mineralogy of the subterranean formations, the presence of hydrocarbons, and inferred rock properties, such as permeability and porosity.

It is recognized that the desired measurement of the physical properties of the earth's subsurface can be best understood by analyzing actual rock samples of the earth's subsurface formations. Such rock samples can be obtained through commercially-available coring services. One of such coring service that has been used extensively for mineral exploration and occasionally for hydrocarbon exploration is described in "Continuous Wireline Core Drilling: An Alternative Method for Oil and Gas Exploration" R. E. Swayne, Drill Bits, Spring 1988 drill bits, pages 7-12. This article also mentions that direct correlations can be made by comparing wireline well logs obtained from the well to measurements made on core samples over the entire length of the well.

Several uses of information obtained from core analysis are described in "Reservoir Description: What Is Needed and When?" by Richardson, et al., published in Symposium on Geology and Reservoir Management, 1986, National Conference on Earth Science, September 1986.

SUMMARY OF THE INVENTION

The present invention provides an exploration method and system that assists an explorationist in obtaining a better understanding of the earth's subsurface. In one embodiment of this invention, core is obtained over substantially the entire length of a wellbore and substantially all the lithologies represented within the core are analyzed within a core analysis facility located adjacent the well to obtain a better understanding of physical properties of the earth's subsurface. Thereafter, a representation, such as a depth correlated record or log, can be generated within the core analysis facility of the earth's subsurface that can be used in making decisions during the drilling of that well and later for exploration and exploitation purposes.

Once a core is removed from the well, connate fluids rapidly evaporate, certain fragile formation materials quickly disintegrate, and core relaxes viscoelastically. The inventors hereof have found that certain of these physical properties change more rapidly than previously thought. By promptly analyzing the core at the well, the core can be analyzed within an acceptably short period of time, with minimal disturbance to the core, and under conditions such that its physical properties will not be substantially different from those of the core when first removed from the well.

DETAILED DESCRIPTION OF THE PREFERRED EMBODIMENT

In accordance with one method of the present invention, core is taken from a well, promptly transported to a core analysis facility adjacent the well, and then substantially all lithologies represented within the core are promptly analyzed to obtain accurate measurements of a plurality of physical properties. These measurements can then be used by an explorationist and/or production personnel to generate a more detailed and accurate understanding of the earth's subsurface, such as by viewing a depth correlated record or log of the measured physical properties.

The method of the present invention involves at least two major components: Drilling/Coring and Core Analysis; both of which will be described below.

Drilling/Coring

Any commercially available drilling and coring rig and associated equipment and supplies can be utilized within the practice of the methods of the present invention. Commercially available rotary coring techniques and wireline provided sidewall coring can be utilized. A particular type of core drilling rig and associated equipment that has been successfully utilized in the practice of this embodiment of the present invention is described in "Continuous Wireline Core Drilling," Swayne, p. 7. High speed, small diameter, low weight-on-bit coring of the type described in the Swayne article is preferred because of a number of reasons. The small diameter, usually less than about 6 in., wellbore produced by this type of drilling does not encounter the expensive and troublesome problems of wellbore stability that is usually experienced with larger diameter wellbores. There is less of a tendency for smaller diameter wellbores to become out of gauge (too large) or for formation material to sluff into the wellbore because with a smaller diameter wellbore, the integrity of the formation is preserved. With the flush-type drillstring used, a small annulus results between the wellbore face and the drillstring. Thus, less drilling fluid is required and less pumping capacity is needed than that usually needed with larger diameter wellbores. Therefore, a more expensive drilling fluid that will cause less damage to the core and formation adjacent the wellbore can be used throughout the entire coring/drilling operation. Further, the coring drillstring usually rotates at greater than about 400 rpm which provides higher penetration rates and does not damage the formation material as much as large diameter core bits rotating at lower rates.

Core Analysis

Figure 1:
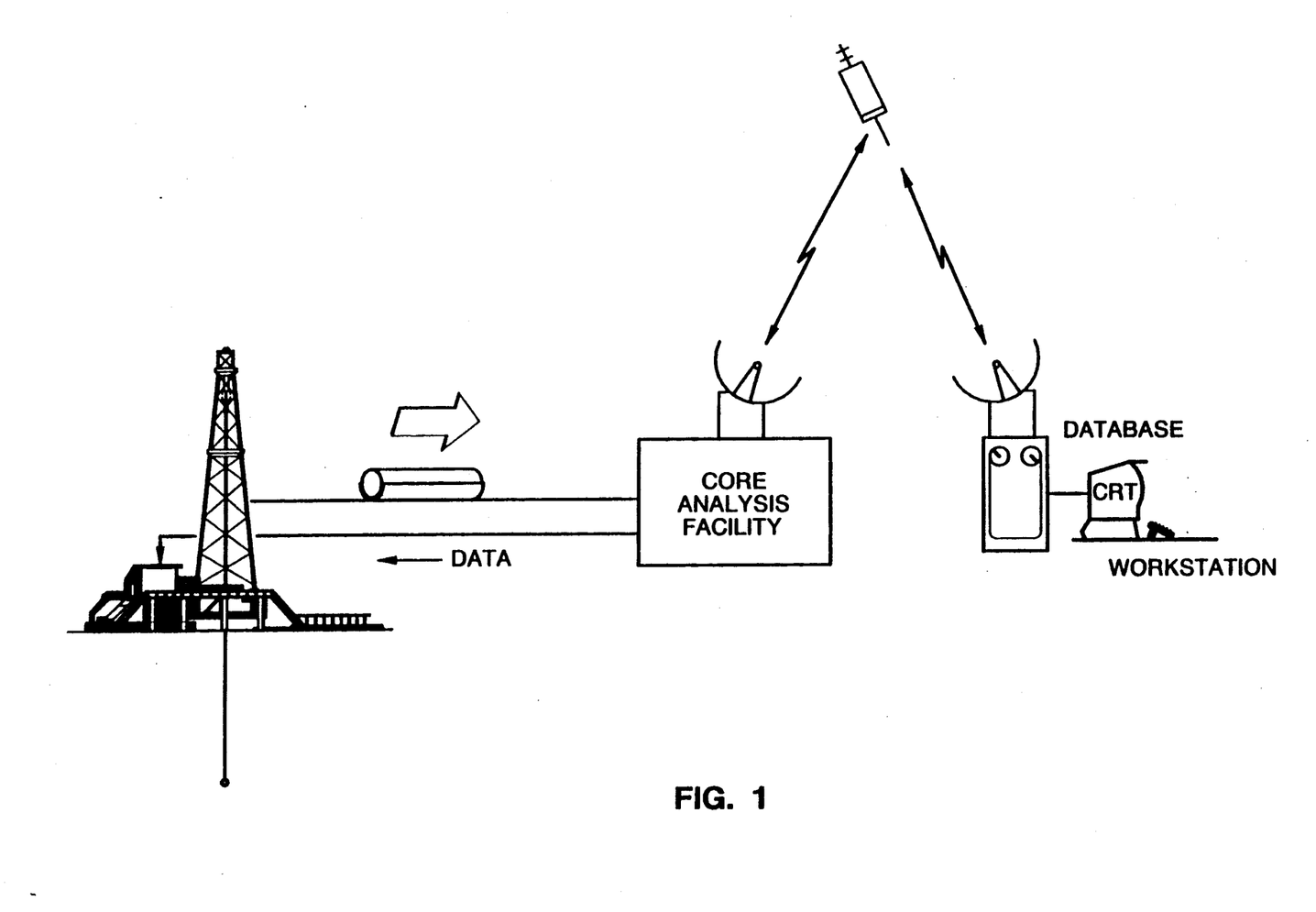
FIG. 1 is a diagrammatic representation of core being withdrawn from a well and being transported to a core analysis facility in accordance with one embodiment of the present invention.

As shown in FIG. 1, in the practice of one embodiment of the present invention, lengths of core, usually 20' or 40', are withdrawn from the wellbore and each length is transported to an adjacent core analysis facility. The core is placed on a carrying rack and passed through a liquid (such as water) bath, wash or spray to remove any drilling fluid or other foreign material from the surface of the core and then passed through an air spray to remove the wash liquid from the core. The wash of liquid and air spray are not mandatory but are preferred to remove any material that could adversely affect a measurement of a particular physical property. Each length of core is cut into appropriate sizes for analysis and storage, such as 3' lengths. Discrete samples are cut from the core for physical property analysis within a discrete sample analysis station, as will be described later.

Figure 2:
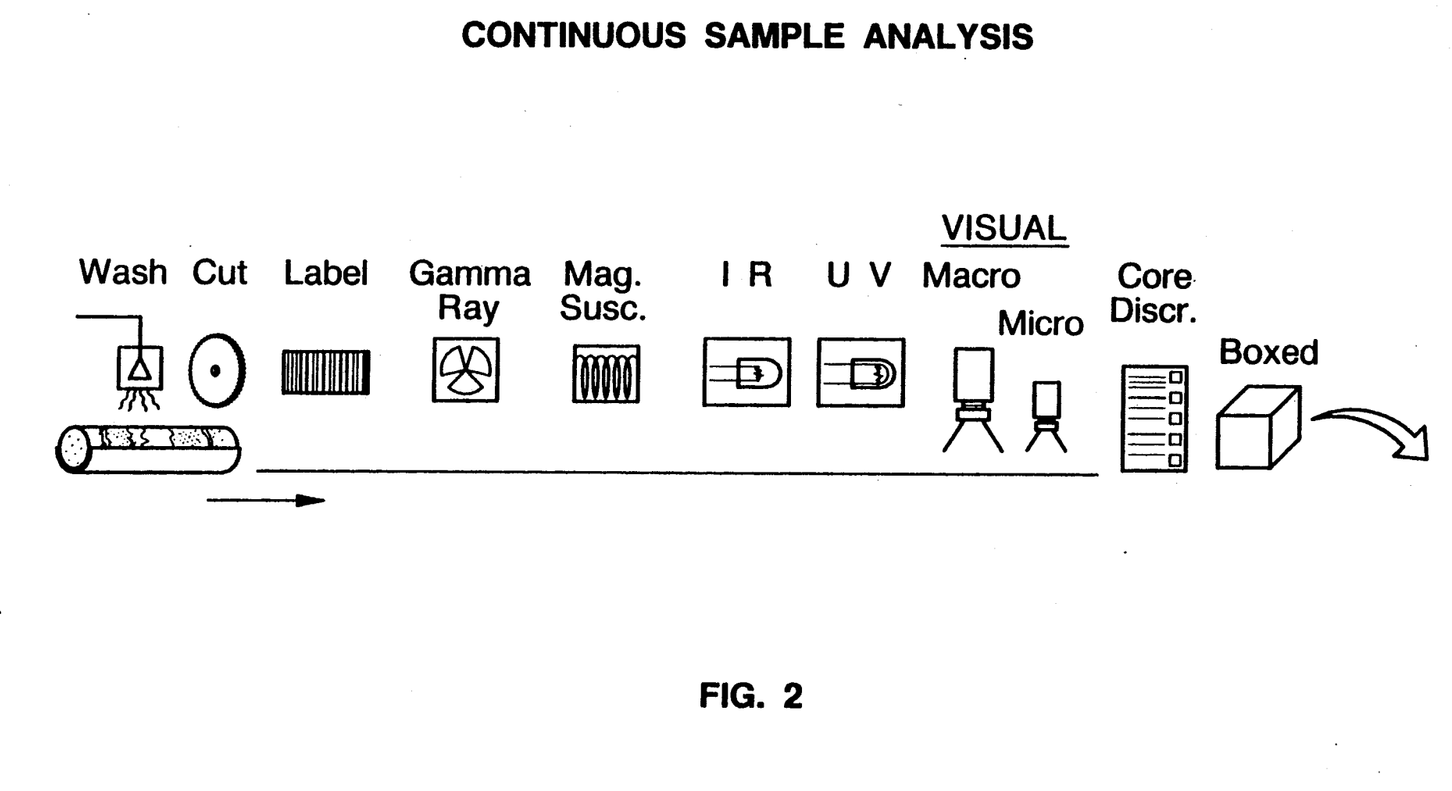
FIG. 2 is a diagrammatic elevational view of a continuous core sampling station within a core analysis facility, integrated as part of the present invention.

The core analysis methodology of the present invention can be divided into two distinct processes: continuous core sample analysis and discrete core sample analysis. In one embodiment of the continuous core sample analysis methodology shown in FIG. 2, after the core has been cut into convenient lengths for analysis and handling, a bar code label is attached to each length for inventory control and then each length is passed through one or more physical property measurement devices to provide the indication of the physical properties of the core. The physical properties that can be measured within this station comprise gamma ray emission which is useful for correlating zones with gamma ray logs from other wells, magnetic susceptibility which is useful for producing a representation of the earth's magnetic characteristics, infrared reflectance which is useful for determining mineralogy, and ultraviolet fluorescence which is useful for detection of hydrocarbons. A visual record of the core is made, such as on a photograph, videotape or laser disk, to record a macroview, such as about 3 in. square visual sample, and a microview of a portion of the macroview, such as by a 10 power microscope.

Figure 3:
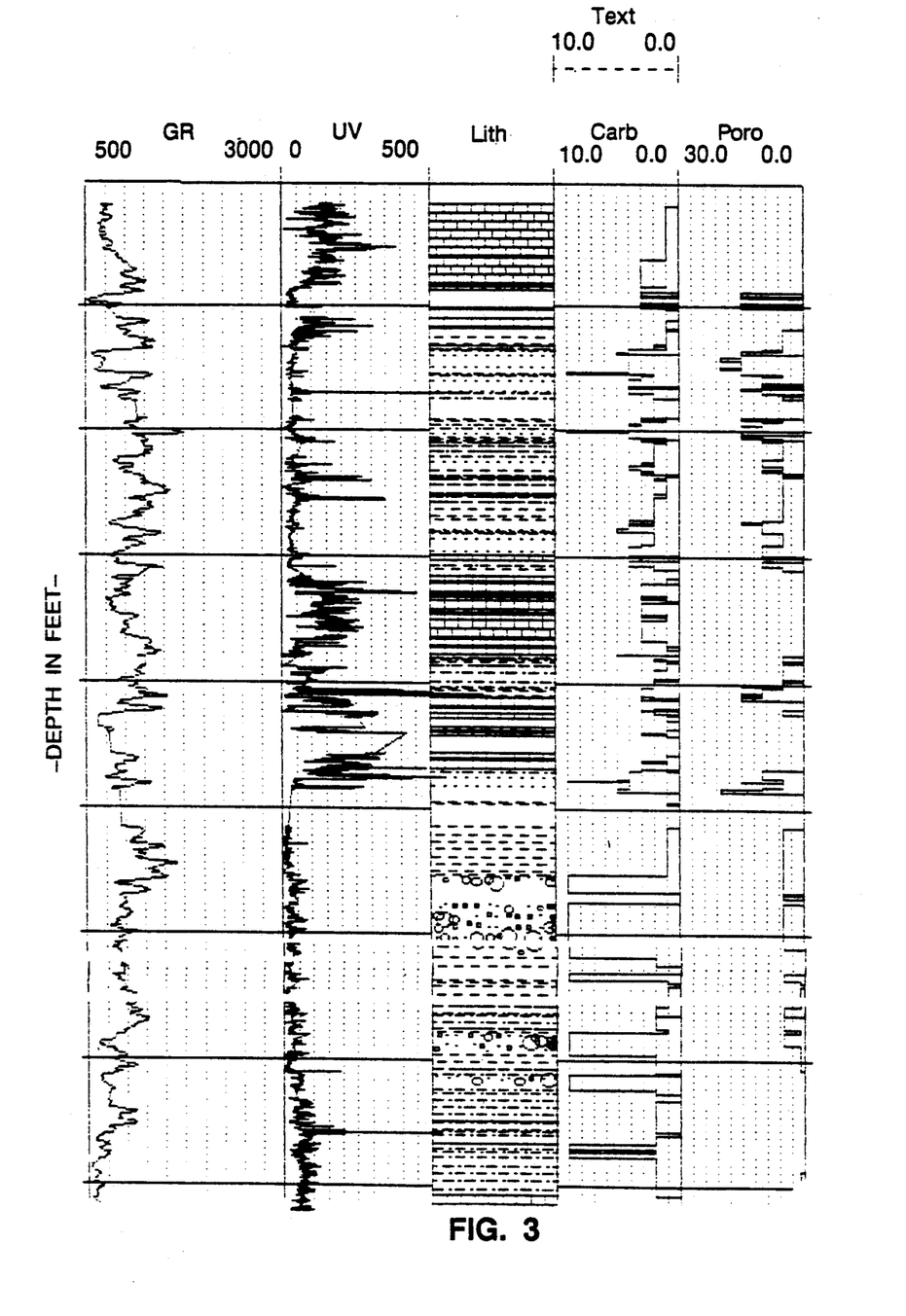
FIG. 3 is a depth correlated log output from one embodiment of a core analysis facility.

The length of core is then passed to a zone where depth correlated core log, record or description is made, usually by a geologist, to record the general lithology type, i.e., carbonate, sandstone, shale, etc., and geological characteristics, such as bedding planes, faulting, dip orientation, depositional environment, depositional history, tectonics, fossil description and the like. An example of a depth correlated log output from such a core analysis facility is shown in FIG. 3, wherein a depth correlated record or log is made in analog form of gamma-ray and ultraviolet fluorescence, a pictorial representation is made of lithology, and estimated measurements are made of carbonate content and porosity. Thereafter, the core can be discarded, boxed and stored on site or all or portions of the core can be transported to a core analysis facility for later analysis and use.

Figure 4:
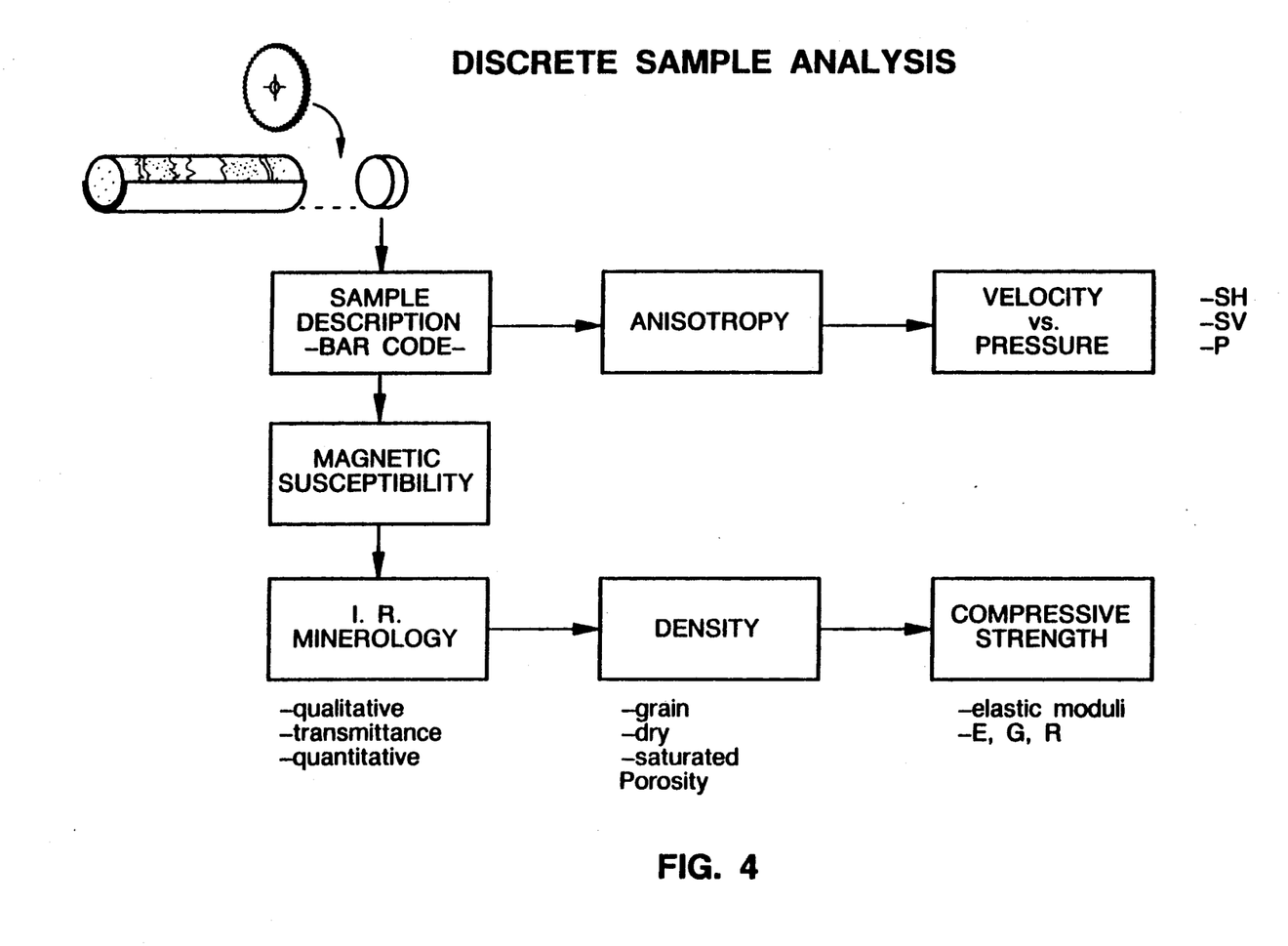
FIG. 4 is a diagrammatic view of a discrete core sampling station within a core analysis facility, integrated as part of the present invention.

In the discrete core sample analysis methodology, discrete samples or discs are taken from the core at predetermined sampling intervals. A sampling interval is at least every lithology change. The interval should be sufficient to adequately represent the physical properties for the wavelength of maximum resolution used for seismic processing, and no greater than every 10'. In one embodiment of the present invention, shown in FIG. 4, at least three disc samples are taken for each lithology and are tested within testing equipment to obtain one or more of the following physical properties: grain density, dry bulk density, saturated bulk density, magnetic susceptibility, mineralogy (infrared), compressive strength, elastic moduli and compressional and shear seismic velocities versus pressure. Having these direct measurements one can calculate other physical parameters of interest. For example, the difference between the dry bulk density and the grain density yields a porosity estimate. Likewise, the difference between the saturated and dry bulk densities yields another estimate of porosity. Further, known combinations of saturated density and seismic velocities yield dynamic elastic moduli, acoustic impedance and reflection coefficients. Piecewise integration of velocity over the depth interval sampled yields an estimate of the two-way traveltime, which can be used to convert the time observed on a seismic section to a true depth. The above described measurements also permit a measurement of P and S wave velocities, birefringence, the magnitude of the difference between the fast and slow shear velocities, and elastic fabric angle. If these measurements are coupled with the sample's measurements (diameter, weight, and length), one can estimate porosity. Also, the difference between saturated and dry density provide a saturated porosity estimate. A depth correlated numerical log of measured properties from the above described discrete sampling facility of FIG. 4 is shown in Table I.

TABLE I

| DEPTH FEET | DENSITIES GM/CM 3 | | POROSITIES % | | VELOCITIES FT/SEC | | | MAG Cgs/ gm X | DIMEN mm | |
|---|---|---|---|---|---|---|---|---|---|---|
| | Grain | Sat | Pycn | Sat | Vp | Vs11 | Vs22 | | dia | len |
| 301.0 | 2.604 | 2.182 | 24.2 | 20.8 | 8056 | 3868 | 4195 | −.01 | 63.1 | 38.2 |
| 312.0 | 2.610 | 2.207 | 24.3 | 23.1 | 8130 | 4693 | 3850 | .07 | 62.9 | 37.9 |
| 321.0 | 2.635 | 2.197 | 25.8 | 24.3 | 8444 | 4022 | 4054 | .14 | 61.9 | 38.0 |
| 340.0 | 2.626 | 2.232 | 23.5 | 22.3 | 8115 | 3649 | 3581 | −.53 | 63.3 | 38.4 |
| 352.0 | 2.635 | 2.232 | 23.0 | 20.2 | 8097 | 5532 | 0 | .25 | 62.9 | 38.2 |
| 365.0 | 2.673 | 2.192 | 26.3 | 22.2 | 7683 | 5388 | 4114 | .12 | 63.3 | 38.1 |
| 375.0 | 2.621 | 2.192 | 22.0 | 14.8 | 7752 | 4647 | 3871 | .26 | 63.2 | 38.2 |
| 385.0 | 2.633 | 2.192 | 24.2 | 19.6 | 8351 | 3927 | 3960 | .22 | 63.4 | 38.5 |
| 395.0 | 2.615 | 2.156 | 25.6 | 21.0 | 8686 | 4321 | 4262 | .22 | 63.1 | 38.2 |
| 405.0 | 2.621 | 2.172 | 26.6 | 24.8 | 8274 | 4209 | 0 | .27 | 63.5 | 38.2 |

Preferable Analysis Methods

Some or all of the measured physical properties from the continuous and the discrete sampling portions of the core analysis facility can be recorded in hardcopy form, visual form or within a memory associated with a digital computer. These physical property measurements can be provided to locations remote from the well site by telephone, fax link, digital communication link and the like. In one embodiment, every day that a well is being drilled, a predetermined subset of the measured physical property data is transmitted via a satellite link to a database within a remote computing facility for an explorationist to develop and refine his/her understanding of the earth's subsurface for that well. Also, other explorationists can access the database for use in improving their understanding of the earth's subsurface at adjacent well sites or well sites completely removed and distinct therefrom. In other words, the measured physical properties can be added into a database which can be used by explorationists to obtain a constantly updated and improving understanding of subsurface phenomena from around the world.

In the analysis of the core, the sample interval has been found to be very important because as more lithologies are not analyzed the interpretations of the data become more generalized and thus more uncertain. If core from a certain zone is analyzed and the other portions of the wellbore are not cored or the core is not analyzed then needed information will be lost. Further, substantially all lithologies within a core need to be analyzed because each lithology affects the time acoustic energy travels through the earth's subsurface. Specifically, if a surface formation's velocity is not measured, then such subsurface formation's impedance must be estimated for use in seismic processing. If the estimate is incorrect, then such error can cause the depth to subsurface reflectors to be in error.

Certain physical properties of the core have been found to change much more rapidly and detrimentally than previously thought with exposure to decompressional, drying and oxidizing conditions and with the passage of time. It is a primary goal of the present invention to promptly analyze the core to obtain a measurement of physical properties approximately equivalent to the physical properties existing at the time of removing the core from the well.

Figure 5:
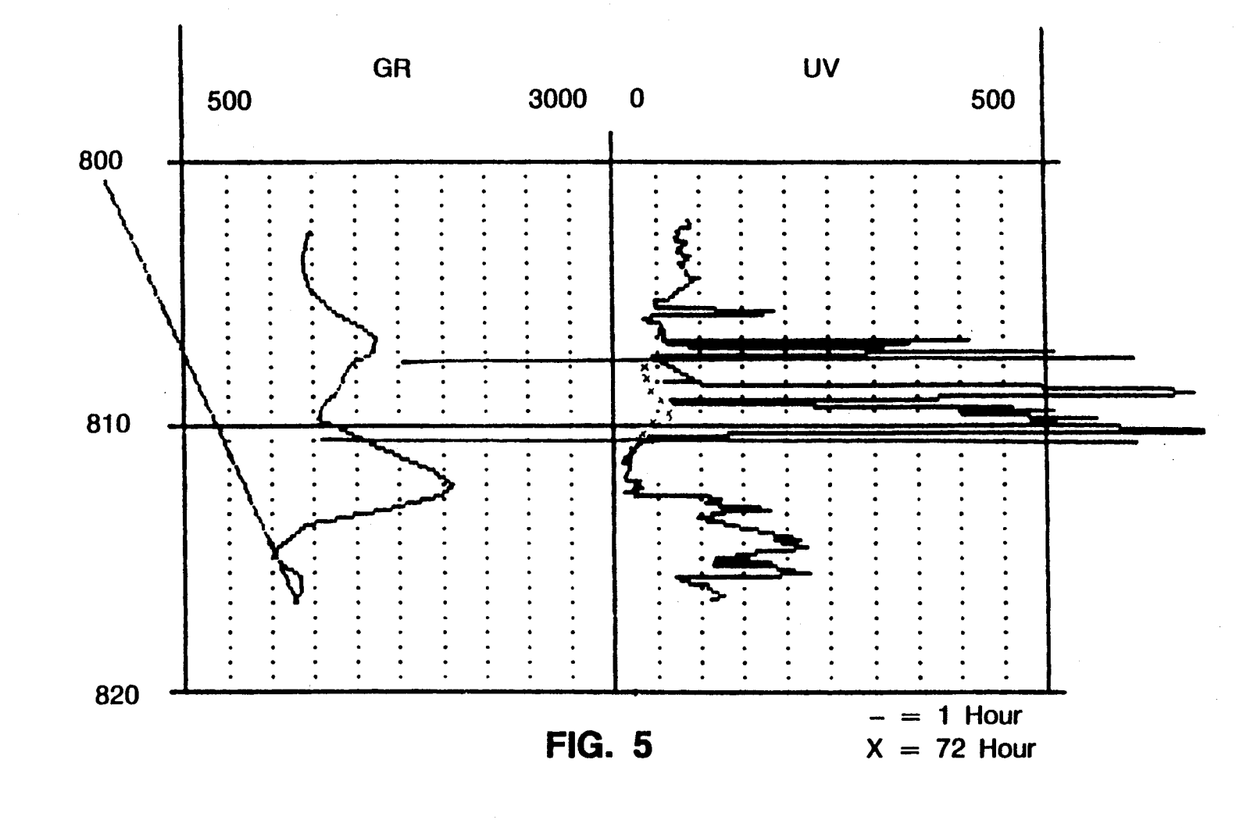
FIG. 5 is a depth correlated ultraviolet log taken at two different times over the same core showing change in the measured ultraviolet response with the passage of time.

For example, hydrocarbons can evaporate quickly so that an ultraviolet fluorescence log taken immediately after the core is removed from a wellbore can show hydrocarbons, yet the same log run as little as 72 hours later will shown no such presence of hydrocarbons. For an example of this, please see FIG. 5. Since in the use of the present invention, one is trying to explore for and hopefully find hydrocarbons, a showing of an oil film on a core at a depth correlated zone can be of significant importance to refining an explorationist's understanding of whether or not hydrocarbons are present, and if so, where did the hydrocarbons come from and where additional hydrocarbons may be. With this information, an explorationist can then make decisions as to whether or not drilling should continue, if so, how much further, and if another well is planned/needed, where to locate the new well. In the past, core taken from a well was transported to a core analysis facility that was remote from the well, and the core analysis usually done several weeks to months later. Thus, valuable data was lost. Yet, with the use of present invention, this valuable data can be generated and used when needed.

Figure 6:
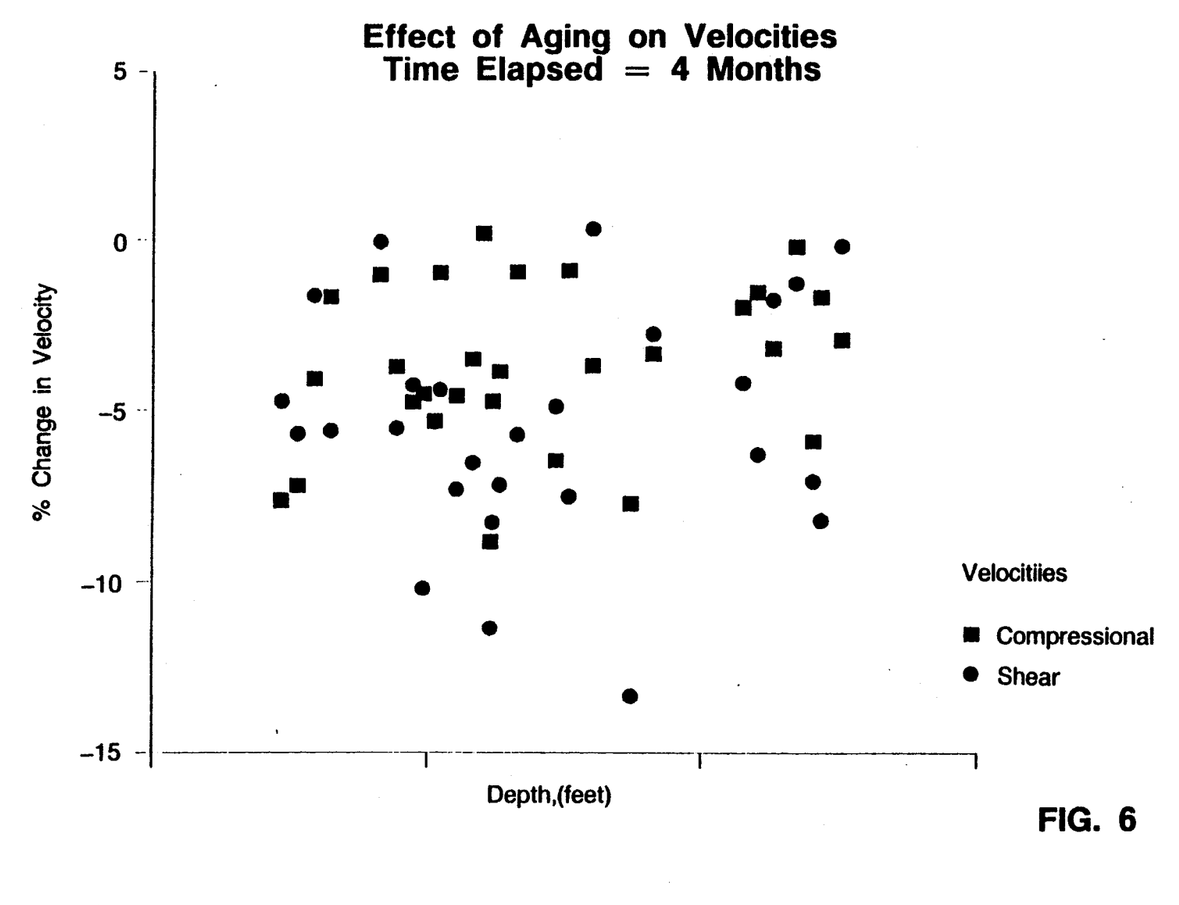
FIG. 6 is a graph of the percent change in measured velocity with the passage of time.

Other properties negatively affected by the passage of time between wellbore removal and analysis are hydrocarbon pyrolysis and pore fluid analysis, compressive strength, and compressional and shear velocities. FIG. 6 shows a graph of a percent change in compressional and shear velocities on a depth correlated scale with the passage of four (4) months between the measurements taken promptly after the core is removed from the well and subsequent measurements taken. These velocity changes are significant because incorrect velocity estimates negatively affect depth estimates to reflectors. For example, a depth estimation made from a seismic plot using a velocity that is 10% slower than the actual velocity yields a time to an event at 10,000' of 2.2 seconds rather than 2.0 seconds. An error of 200 milliseconds in target depth can translate to a misidentified event and a projected additional penetration of about 1000' to 1500'. Such errors negatively impact the economics of finding a desired zone and the certainty of attaining the drilling objectives.

Further, velocity estimates for shallower depths are nonexistent or, at best, poorly constrained. For example, a shallow high velocity zone was cored and the measured velocities for the zone proved to be markedly faster than the estimated velocities used in processing the seismic section. The original estimates led to a predrilling depth estimate of the objective zone of 7900'. By using the actual measured velocities of the core obtained from the core analysis facility adjacent the well, the seismic section was reprocessed and the objective zone was estimated to be at 6000'. The drill bit later cored the objective zone at 6030'.

This use of the velocity data permits one to stop drilling if desired to forego the cost of having to drill to the originally planned 7900'. Further, usually a vertical seismic profile would have been obtained using a wireline logging tool to confirm the penetration of the objective zone; however, with the confidence gained from the on-site core analysis, the operator was able to forego this additional expense. As an added point, similar drilling estimates to objective zones can be done using velocity logs; however, such logging is not preferred, compared to the on-site core analysis of the present invention, because to use such logging methods the drilling must be stopped, marginally stable wellbores can be damaged and collapse, and additional time and money is needed to acquire and process these logs. The present invention provides a method to obtain needed physical property measurements from core as an integral part of the drilling process.

Certain formation materials, such as shales, disintegrate very quickly with exposure to air, vibration and release from their in-situ conditions. Usually, shales are not analyzed at a remote core analysis facility because the shales have disintegrated; thereby valuable information is lost. Therefore, it is imperative to analyze these formation materials on-site if one hopes to obtain any meaningful measurements of their physical properties and description of their characteristics.

Use of the Measured Properties

The following discussion is provided to permit a better understanding of additional uses of the information generated within the core analysis facilities, in accordance with the present invention.

As described above, the physical properties of the core material can be used at the well site to recalculate the depth of reflectors, i.e., horizons to be drilled, and the distance to target or total depth (TD) of the well. In the past, the production personnel drilling the well had a rough guess of the depth to which they are to drill to reach a particular desired horizon. However, that horizon is almost always estimated from offset well logs and/or seismic data, which in turn is heavily dependent upon assumed rock properties and velocities. With the timely core analysis provided by the preset invention, the drilling personnel can determine whether or not they have passed through a particular horizon of interest and at what depth a particular horizon was passed through. Also, a prediction can be timely made of how much longer a particular formation is to be drilled before a formation change is expected, so the drilling personnel can determine whether or not to make a bit change and/or a fluid change and when to make such change(s).

Drill bit performance can be determined by knowing the lithology and compressive strength of the formation from the timely core analysis and knowing the rate of penetration of that bit through the formation, thus one can monitor the degradation of bit performance caused by bit wear and/or bit failure. Also, one can establish an understanding of how well a particular drill bit drills through a particular formation material. In the past, these types of accurate determinations could not be made because prompt, on-site instrumental core analysis was not available.

Because of timely core analysis, information obtained from the well can be quickly utilized for development or refinement of additional exploitation, exploration, well drilling, and well completion plans for other wells in the same or other areas. The density data and magnetic susceptibility data can be used to reprocess gravity and magnetic surveys. Timely analysis can shorten play evaluation time which leads to a higher efficiency by exploration personnel. Thus, rapid determinations can be made of whether or not to bid on a concession/lease, how much to bid, if and where additional wells are to be drilled within the concession/lease and the like.

Figure 7:
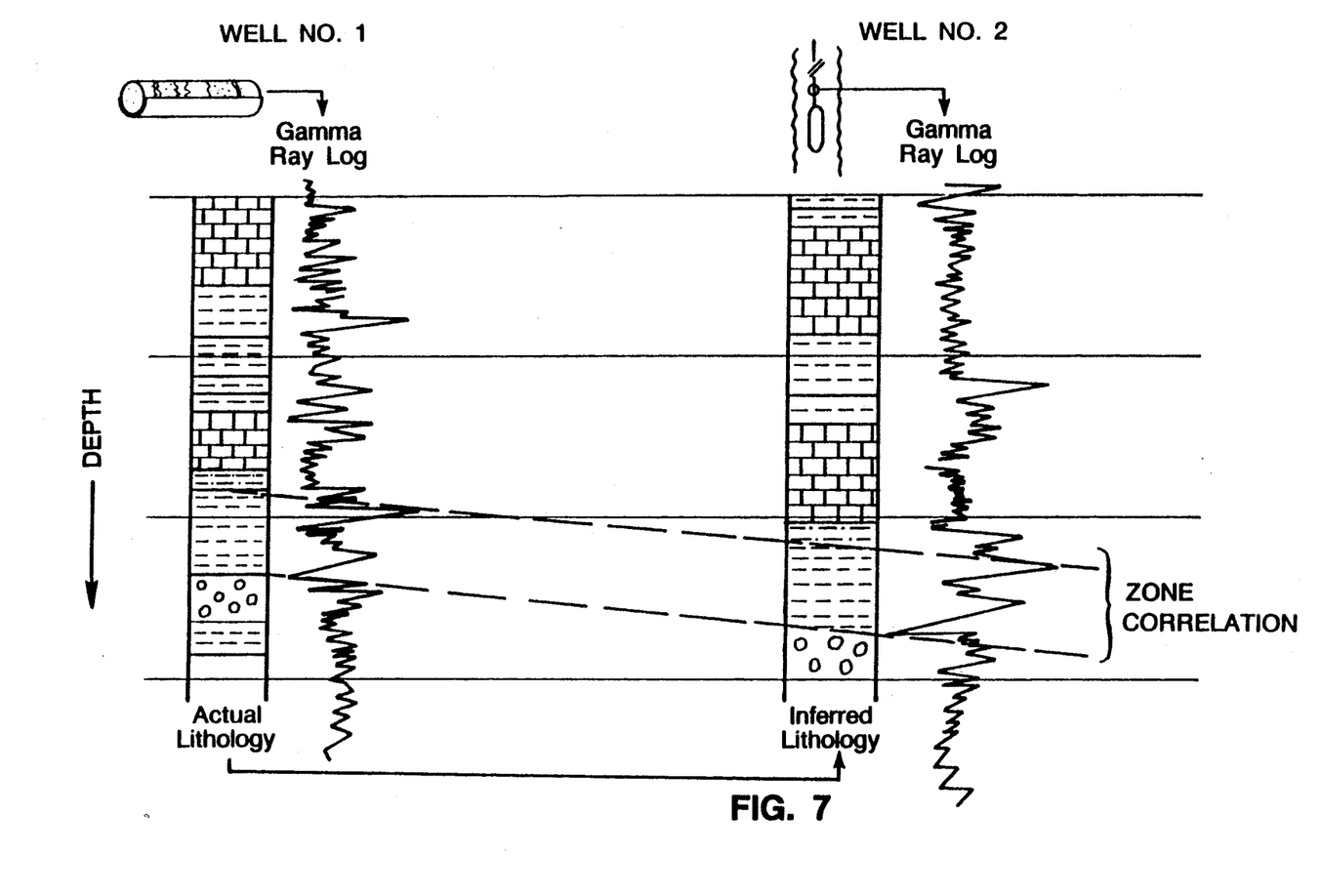
FIG. 7 is a diagrammatic representation of correlating a log obtained from core analysis of the present invention to a conventional log obtained from an offset well.

A form of logging, called inverse logging, can be accomplished wherein a well is drilled, core obtained therefrom and analyzed in accordance with the present invention. Thereafter, the depth correlated log of the core can be correlated to other logs, such as a gamma ray log, obtained from offset wells to establish the location and depth of the same zones penetrated by both wellbores. Further, from the logs generated by way of the present invention, the lithology and other physical properties can be reasonably inferred at the offset well(s). An illustration of this technique is diagrammatically shown in FIG. 7.

By having substantial quantities of core, from a well, such as core from substantially the entire length of the well and having that core analyzed on-site, more of the entire picture of the depositional environment of the earth's subsurface can be determined. The depositional environment will include whether or not there were beaches, streams, dunes, and the like present, and have any alterations taken place. The tectonic history can be determined as well as paleontological sequencing. The diagenetic history can be determined as well as the types and distribution of fossils. Depositional environment, rock fabrics, diagenetics, burial history, the presence of source, reservoir and cap rocks, can also be determined. Reservoir quality and characteristics, rock type and distribution, can all be determined directly from the core on site in such a manner that these properties can provide information directly to the explorationist to better refine and evaluate the subsurface model. The porosity, fracture concentration and orientation can provide indications of the areal and vertical continuity of a basin.

Future stimulation procedures for the cored well, such as fracturing, acidizing and the like, can be more accurately designed because actual core is analyzed to obtain the necessary inputs, such as formation parting pressures, permeability, Poisson's ratio and Young's moduli and the like.

Wherein the present invention has been described in particular relation to the drawings attached hereto, it should be understood that other and further modifications, apart from those shown or suggested herein, may be made within the scope and spirit of the present invention.

What is claimed is:

1. A method of producing a depth correlated record of the earth's subsurface using core cuts as a well is being drilled, comprising:
   (a) within a core analysis facility adjacent the well, analyzing substantially all lithologies represented within the core taken from substantially the entire length of the wellbore to obtain a measurement of physical properties thereof promptly after the core is removed from the well; and
   (b) producing a depth correlated record of the physical properties.

2. The method of claim 1 wherein the physical properties are selected from the group consisting of gamma ray, infrared absorption, infrared reflectance, magnetic susceptibility, ultraviolet fluorescence, saturated density, dry density, grain density, porosity, shear acoustic velocity, compressional acoustic velocity, elastic moduli and compressive strength.

3. The method of claim 1 wherein core is obtained from substantially the entire length of the well and is provided to the core analysis facility.

4. The method of claim 2 wherein the measurement of magnetic susceptibility is used to produce a representation of the earth's magnetic characteristics.

5. The method of claim 1 wherein the depth correlated record of at least one physical property is correlated to a depth correlated log obtained from another well.

6. A depth correlated record of the physical properties made in accordance with claim 1.

7. A core analysis facility for use adjacent a well to produce a depth correlated record of the earth's subsurface, comprising:
   means for analyzing substantially all lithologies represented within a core removed from substantially the entire length of a well to obtain a measurement of physical properties thereof promptly after the core is removed from the well, and
   means for producing a depth correlated record of the physical properties.

8. The system of claim 7 wherein the physical properties are selected from the group consisting of gamma ray, infrared absorption, infrared reflectance, magnetic susceptibility, ultraviolet fluorescence, grain density, dry density, saturated density, porosity, shear acoustic velocity, compressional acoustic velocity, elastic moduli and compressive strength.

9. A method of exploring for hydrocarbons, comprising:
   (a) developing a representation of the earth's subsurface;
   (b) developing a well drilling plan from the representation of the earth's subsurface;
   (c) drilling a wellbore to penetrate the earth's subsurface in accordance with the drilling plan;
   (d) obtaining a core over substantially the entire length of the wellbore;
   (e) analyzing substantially all lithologies represented within the core at a location adjacent the wellbore to obtain a plurality of physical properties thereof;
   (f) revising the representation of the earth's subsurface from the obtained plurality of physical properties;
   (g) revising the drilling plan for the wellbore in response to the revisions in the representation of the physical properties of the earth's subsurface; and
   (h) drilling the wellbore in accordance with the revised drilling plan.

10. The method of claim 9 wherein the plurality of properties include compressive strength and porosity.

11. The method of claim 9 wherein the representation of the earth's subsurface comprises a seismic section.

12. A method of exploring for hydrocarbons comprising:
   (a) obtaining a depth correlated record of at least one physical property of a core taken from substantially the entire length of a wellbore analyzed at a core analysis facility adjacent a first well from which the core was obtained and analyzed promptly after the core is removed from the first well;
   (b) obtaining a depth correlated record of the at least one physical property from a wireline log passed through a second well; and
   (c) comparing similar indicated subsurface features from the record of step (a) to a record of step (b).

13. The method of claim 12 wherein the at least one physical property is natural gamma ray radiation.

14. The method of claim 12 and including:
   (d) developing an inferred lithology log for the second well from the depth correlated record of at least one physical property of the first well.

* * * * *